(12) United States Patent
Slizynski et al.

(10) Patent No.: US 9,037,227 B2
(45) Date of Patent: May 19, 2015

(54) USE OF IMPEDANCE TECHNIQUES IN BREAST-MASS DETECTION

(76) Inventors: Roman A. Slizynski, Foothill Ranch, CA (US); David J. Mishelevich, Playa del Rey, CA (US)

( * ) Notice: Subject to any disclaimer, the term of this patent is extended or adjusted under 35 U.S.C. 154(b) by 720 days.

(21) Appl. No.: 12/874,192

(22) Filed: Sep. 1, 2010

(65) Prior Publication Data

US 2011/0054344 A1  Mar. 3, 2011
US 2011/0230784 A2  Sep. 22, 2011

Related U.S. Application Data

(60) Provisional application No. 61/238,949, filed on Sep. 1, 2009.

(51) Int. Cl.
*A61B 5/00* (2006.01)
*A61B 5/053* (2006.01)
*A61B 5/05* (2006.01)

(52) U.S. Cl.
CPC ............... *A61B 5/4312* (2013.01); *A61B 5/053* (2013.01)

(58) Field of Classification Search
CPC .... A61B 5/4312; A61B 5/053; A61B 5/0536; A61B 5/0537; A61B 2017/00026
USPC ...................... 600/382, 407, 442, 547; 606/34
See application file for complete search history.

(56) References Cited

U.S. PATENT DOCUMENTS

| | | | |
|---|---|---|---|
| 4,537,203 A * | 8/1985 | Machida | 600/547 |
| 5,810,742 A * | 9/1998 | Pearlman | 600/547 |
| 6,351,666 B1 | 2/2002 | Cuzick | |
| 6,425,875 B1 | 7/2002 | Reifman | |
| 6,922,586 B2 * | 7/2005 | Davies | 600/547 |
| 6,993,383 B2 * | 1/2006 | Assenheimer | 600/547 |
| 7,141,019 B2 | 11/2006 | Pearlman | |
| 7,302,292 B2 | 11/2007 | Ginor | |
| 7,630,759 B2 * | 12/2009 | Davies | 600/547 |
| 7,865,236 B2 * | 1/2011 | Cory et al. | 600/547 |
| 8,103,337 B2 * | 1/2012 | Graovac et al. | 600/547 |
| 8,275,453 B2 * | 9/2012 | Davies | 600/547 |
| 8,280,504 B2 * | 10/2012 | Davies | 600/547 |
| 2002/0183645 A1 * | 12/2002 | Nachaliel | 600/547 |
| 2004/0068297 A1 * | 4/2004 | Palti | 607/2 |
| 2004/0077944 A1 * | 4/2004 | Steinberg et al. | 600/436 |

(Continued)

OTHER PUBLICATIONS

Gabriel et al. "The Dielectric Properties of Biological Tissue: II. Measurements in the Frequency Range 10 Hz to 20 GHz." Phys. Med. Biol. 41. p. 2251-2269. 1996.*

(Continued)

*Primary Examiner* — Adam J Eiseman

(57) ABSTRACT

A device is described for measuring electrical characteristics of biological tissues with plurality of electrodes and a processor controlling the stimulation and measurement in order to detect the presence of abnormal tissue masses in the breast and determine probability of tumors containing malignant cancer cells being present in a breast. The device has the capability of providing the location of the abnormality, at least to the quadrant. The method for measuring electrical characteristics includes placing electrodes and applying a voltage waveform in conjunction with a current detector. A mathematical analysis method is then applied to the collected data, which computes spectrum of frequencies and correlates magnitudes and phases with given algebraic conditions to determine mass presence and type.

17 Claims, 5 Drawing Sheets

(56) References Cited

U.S. PATENT DOCUMENTS

| | | | | |
|---|---|---|---|---|
| 2004/0152997 | A1* | 8/2004 | Davies | 600/547 |
| 2004/0243018 | A1* | 12/2004 | Organ et al. | 600/547 |
| 2005/0065418 | A1* | 3/2005 | Ginor | 600/345 |
| 2007/0293783 | A1 | 12/2007 | Ginor et al. | |
| 2012/0065539 | A1 | 3/2012 | Slizynski et al. | |

OTHER PUBLICATIONS

Alexander Stojadinovic, et al, "Electrical Impedance Scanning for the Early Detection of Breast Cancer in Young Women: Preliminary Results of a Multicenter Prospective Clinical Trial," Journal of Clinical Oncology, vol. 23, No. 12, Apr. 20, 2005: 2703-2715. [American Society of Clincal Oncology, Alexandria, VA, USA].*

Ruigang Liu, Xiuzhen Dong, Feng Fu, Fusheng You, Xuetao Shi, Zhenyu Ji, Kan Wang, "Multi-frequency parameter mapping of electrical impedance scanning using two kinds of circuit model," Physiological Measurement: Jul. 2007 vol. 28 Start p. S85. [IOP Publishing, Bristol, UK].

Tyna A Hope and Siân E Iles, "The use of electrical impedance scanning in the detection of breast cancer," Breast Cancer Res. 2004; 6(2):69•74. [BioMed Central, Springer, New York City, NY, USA].

J. Jossinet and B. Lavandier, "The discrimination of excised cancerous breast tissue samples using impedance spectroscopy," Bioelectrochemistry and Bioenergetics, vol. 45, Issue 2, May 1998, pp. 161-167 [Elsevier, Amsterdam, Netherlands].

Arum Han, Lily Yang and A. Bruno Frazier, "Quantification of the Heterogeneity in Breast Cancer Cell Lines Using Whole-Cell Impedance Spectroscopy," Clinical Cancer Research 13, 139, Jan. 1, 2007. doi: 10.1158/1078-0432.CCR-06-1346. [American Association for Cancer Research, Philadelphia, PA, USA].

Kan Wang, Ting Wang, Feng Fu, Zhen-Yu Ji, Rui-Gang Liu, Qi-Mai Liao and Xiu-Zhen Dong, "Electrical impedance scanning in breast tumor imaging: correlation with the growth pattern of lesson," Chinese Medical Journal 2009; 122(13):1501-1506. [Chinese Medical Society, Beijing, P.R. China].

T. Morimotoa, Y. Kinouchib, T. Iritanic, S. Kimuraa, Y. Konishia, N. Mitsuyamaa, K. Komakia and Y. Mondena, "Measurement of the Electrical Bio-Impedance of Breast Tumors,", European Surgical Research vol. 22, No. 2 1990;22:86-92 (DOI: 10.1159/000129087). [Karger, Basel, Switzerland].

Alexander Stojadinovic Aviram Nissan, Craig D. Shriver, Sarah Lenington, and David Gur, Electrical Impedance Scanning for Breast Cancer Risk Stratification in Young Women, Hermann Scharfetter, Robert Merva (Eds.): ICEBI 2007, IFMBE Proceedings 17, pp. 675-678, 2007.

* cited by examiner

USE OF IMPEDANCE TECHNIQUES IN BREAST-MASS DETECTION

CROSS REFERENCE TO RELATED APPLICATIONS

This patent application claims priority to Provisional Patent Application, 61/238,949, filed Sep. 1, 2009.

INCORPORATION BY REFERENCE

All publications and patent applications mentioned in this specification are herein incorporated by reference in their entirety to the same extent as if each individual publication or patent application was specifically and individually indicated to be incorporated by reference.

REFERENCES

[1] Ruigang Liu, Xiuzhen Dong, Feng Fu, Fusheng You, Xuetao Shi, Zhenyu Ji, Kan Wang, *Multi-frequency parameter mapping of electrical impedance scanning using two kinds of circuit model*. Physiological Measurement: July 2007 Volume: 28 Start Page: S85.
[2] Tyna A Hope 1 and Siân E Iles2, *The use of electrical impedance scanning in the detection of breast cancer*. Breast Cancer Res. 2004; 6(2): 69-74.
[3] J. Jossinet and B. Lavandier, *The discrimination of excised cancerous breast tissue samples using impedance spectroscopy*, Bioelectrochemistry and Bioenergetics, Volume 45, Issue 2, May 1998, Pages 161-167
[4] Arum Han, Lily Yang and A. Bruno Frazier, *Quantification of the Heterogeneity in Breast Cancer Cell Lines Using Whole-Cell Impedance Spectroscopy*, Clinical Cancer Research 13, 139, Jan. 1, 2007. doi: 10.1158/1078-0432. CCR-06-1346
[5] Alexander Stojadinovic, Aviram Nissan, Zahava Gallimidi, Sarah Lenington, Wende Logan, Margarita Zuley, Arieh Yeshaya, Mordechai Shimonov, Moshe Melloul, Scott Fields, Tanir Allweis, Ron Ginor, David Gur, and Craig D. Shriver, *Electrical Impedance Scanning for the Early Detection of Breast Cancer in Young Women: Preliminary Results of a Multicenter Prospective Clinical Trial*, Journal of Clinical Oncology, Volume 23, Number 12, Apr. 20, 2005: 2703-2715
[6] WANG Kan, WANG Ting, FU Feng, JI Zhen-yu, LIU Rui-gang, LIAO Qi-mei and DONG Xiuzhen, *Electrical impedance scanning in breast tumor imaging: correlation with the growth pattern of lesion*, Chinese Medial Journal 2009; 122(13):1501-1506
[7] T. Morimotoa, Y. Kinouchib, T. Iritanic, S. Kimuraa, Y. Konishia, N. Mitsuyamaa, K. Komakia, Y Mondena, *Measurement of the Electrical Bio-Impedance of Breast Tumors*, European Surgical Research Vol. 22, No 2, 1990; 22:86-92 (DOI: 10.1159/000129087).
[8] Alexander Stojadinovic, M.D., Aviram Nissan, M.D., Craig D. Shriver, M.D., Sarah Lenington, Ph.D., David Gur, Sc.D, *Electrical Impedance Scanning for Breast Cancer Risk Stratification in Young Women*, Hermann Scharfetter, Robert Merva (Eds.): ICEBI 2007, IFMBE Proceedings 17, pp. 675-678, 2007.

FIELD OF THE INVENTION

The application of a signal to tissue and differentiating tissue characteristics such as the presence of benign or malignant growths from normal tissue based on impedance characteristics.

BACKGROUND OF THE INVENTION

Bio-impedance of breast tumors has been a source for numerous scientific research studies since discovery of electricity by Volta in 1800. It was the Cole brothers (in 1930) who mathematically and physically described dielectric properties. Cole-Cole equations are used in bio-impedance analysis. Since the late 1960's, bio-impedance analysis has benefited from the advent of microprocessors and digital signal processing.

The method can also be used to characterize biological tissue electrical properties in many different applications including blood analysis, body muscle and fat content as well as in estimating the length of the root canal in teeth see U.S. Pat. No. 6,425,875 "Method and device for detection of tooth root apex."

Electrical Impedance Scanning (EIS) has been described in literature [1] [2] and machines have been built to be used on patients. The EIS of the breast relies on body transmission of alternating electricity using an electrical patch attached to the arm and a hand-held cylinder. The electrical signal flows through the breast where it is then measured at skin level by a probe placed on the breast. Examples of such devices are the T Scan 2000 from Mirabel Medical Systems, which has been cleared by the FDA for adjunctive diagnosis in conjunction with mammography, and the follow-on T Scan 2000 ED. Mirabel devices are covered under multiple patents among which are Andrew L. Pearlman (U.S. Pat. No. 7,141,019), Ron Ginor (U.S. Pat. No. 7,302,292) and Ginor and Nachaliel (U.S. Patent Application Pub. No. 2007/0293783). Other devices are the one from Biofield Corp. (Cuzick et al, U.S. Pat. No. 6,351,666), and the device of Richard J. Davies (U.S. Pat. Nos. 6,922,586 and 7,630,759).

The benefits of having a non-mammographic mechanism to screen for patients whose age is less that age 50 are significant. Below age of 40, radiation from use of screening mammography will cause more cancer than it saves. Between 40 and 50 there is a break even where one saves approximately as many of cancers caused. Above 50 years of age mammography works well because a tumor contrasts well against normal breast tissue. Below age 40 the density of the breast tissue is so high that it difficult to impossible to differentiate from a tumor. The same is not quite as true for women in the age group of 40 to 50 but the problem with mammographic differentiation between normal breast tissue and cancer remains.

Asymptomatic young women under the age of 40 are not routinely screened (in the United States) but instead depending on breast self examination (BSE) and clinical breast examination (CBE). Carcinoma of the breast is generally more aggressive in younger women. The availability of a diagnostic test that does not involve radiation would be of significant benefit.

Mammograms only demonstrate presence of calcium and not all DCIS masses have calcium deposits. MRI and PET only detect increases in vascularity which may or may not be present. One consideration in mammography is that the results are not necessarily stable; some 30% of "cancer" detected on mammography disappears.

Another factor is the detection of breast cancer and other abnormalities is the cost of doing procedures. It would of significant benefit, particularly in developing countries, to have a low cost procedure. Of course, lower cost and resulting wider availability is important in developed nations as well.

SUMMARY OF THE INVENTION

Breasts can be examined using an electrical impedance scanning method, which has been previously described in many publications [1] [2] [3]. In this novel invention, the method is improved to quickly scan through multiple frequencies by using a complex waveform containing even and odd harmonics across several decades of frequencies.

Uses are:
1. Detection of Ductal Carcinoma In Situ (DCIS) other malignant tumor masses, or benign breast masses
2. Follow up of changes in masses over time
3. Assess effectiveness of treatment to eradicate DCIS or other tumors.

The invention provides significant benefits, first by avoiding use of radiation which can generate the cancers that mammography that the test is meant to detect and perhaps other cancers and second by offering a low-cost diagnostic test and tracking vehicle.

DETAILED DESCRIPTION OF THE INVENTION

The amplitude and phase of several harmonics within a range of frequencies creates a signature of the breast growths allowing differentiation of benign and malignant masses. Our invention is novel in that it differentiates normal from abnormal tissue based on observing secondary effects of changes in dielectric properties due to increased numbers of cells based on phase and amplitude of multiple levels of harmonics without the necessity to measure absolute capacitance and resistance values. The invention allows differentiation of benign masses (e.g., tumor or infections) versus malignant masses versus other cellular changes. Our approach is not impacted by patient to patient differences.

Other impedance-related approaches (e.g., those referenced above from Mirabel Medical Systems, Biofield, and Davies) depend on measuring absolute capacitive and absolute resistive properties to compute the Cole-Cole function shape. Measuring absolute values is difficult and inherently error prone, especially since they will vary from patient to patient.

Figure 1:
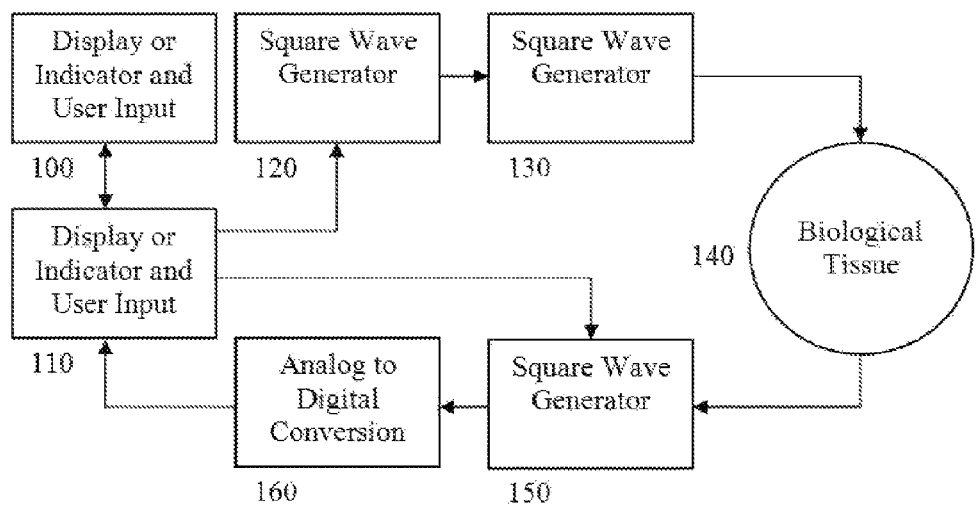
FIG. 1 shows a block diagram of the impedance application system.
Figure 11:
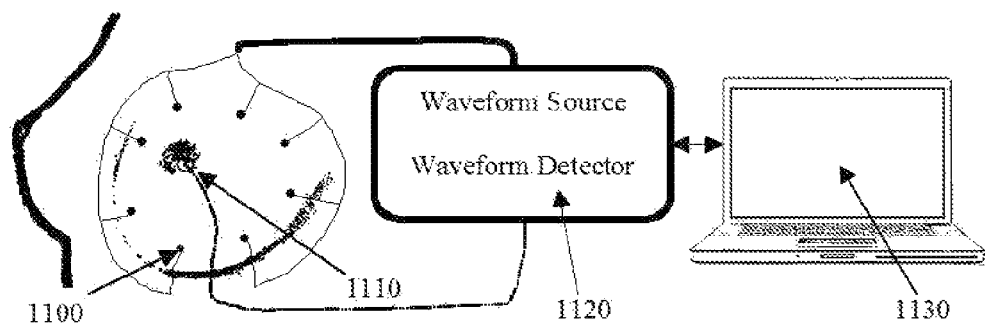
FIG. 11 illustrates the breast cancer test configuration.

An embodiment of a suitable device is shown in the Block Diagram of FIG. 1, which illustrates the block diagram of the invention for breast-mass detection. After the unit powers up through the use of user interface 100, the microprocessor 110 will load the characteristics of the desired square wave to the generator 120. If another wave type were used (e.g., sine or saw tooth), generator 120 would generate that wave type. As commanded by the medical professional through the input interface 100, the microprocessor 110 will start coherent sampling by synchronizing the waveform generation 120 and waveform capture 150. Output stage 130 assures proper voltage levels and their rising and falling edges. The output stage 130 also distributes the signal to multiple electrodes as shown in FIG. 11. Microprocessor 110 controls the main frequency and triggers the current capture 150. The biological tissue 140 is the breast under examination. The sampled current 150 is digitized by Analog to Digital Converter (ADC) 160. A Fast Fourier Transform (FFT) is computed by microprocessor 110 on $2^n$ samples received from ADC 160. For practical considerations, the n should be equal or greater than 8. Typically it would be 12, but with microprocessor advances this can be increased for better accuracy. The resulting FFT data with its magnitude and phase are compared by the microprocessor 110 with the identifying references stored in it. The references may include markers identifying benign or malignant tumors including their relative position to a probes being tested. All the conclusions of testing by the microprocessor 110 are sent to the display 100 to inform the medical professional. The circuit requires coherent source and sampling conditions to achieve the spectral resolution needed to precisely identify changes in amplitudes and phases caused by masses, including growing cancer cells. Coherent sampling is superior over any type of data windowing or interpolation. A wide spectral band is used from around 20 kHz to several MHz with odd harmonics. The non-linearities in the tissue will contribute to generation of even harmonics at much smaller amplitude. Our invention can be used in the ranges of 10 kHz to 1 MHz, or from 1 MHz to approximately 100 MHz, and from 100 MHz to 10 GHz.

Figure 2:
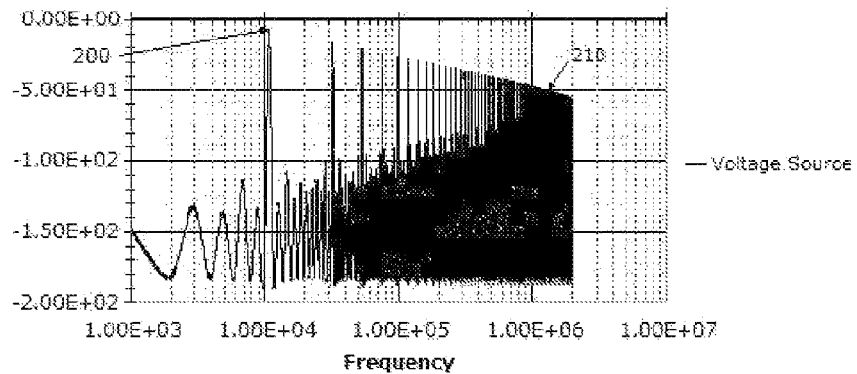
FIG. 2 illustrates the source waveform with all even and odd harmonics.

In one embodiment, the square wave main frequency 200 in FIG. 2 is set to 10.74219 kHz. This satisfies the coherency condition of 11 cycles, 4096 samples and 250 ns sampling. It places the $93^{rd}$ 210 harmonic at 999.0234 kHz. This setting takes into computation 48 harmonics. Research papers have indicated 100 kHz to 1 MHz to be affected by growing tumor cells [4] [5]. The square wave rising and falling edges were set to 250 ns giving odd harmonic content.

Figure 3:
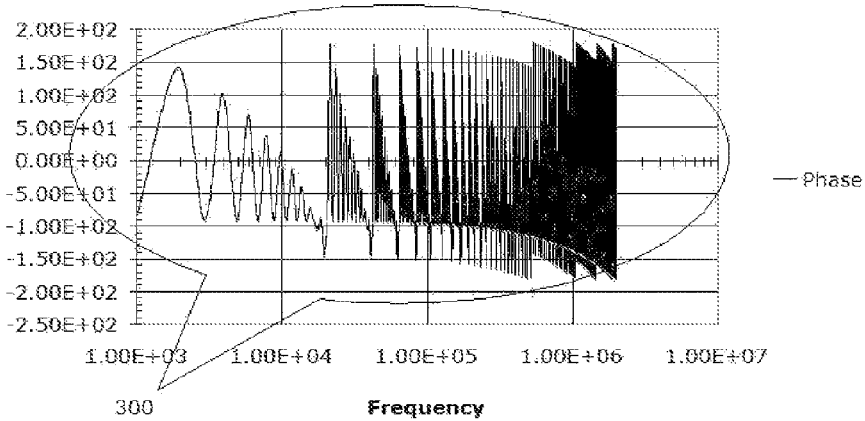
FIG. 3 shows the phase of the source waveform.

All harmonics in the band of the source square wave, as shown with their magnitude in FIG. 2 and the phase in FIG. 3, are used in the computation. The results of magnitude and phase changes 300 in FIG. 3 are compared with the set of the reference amplitudes and phases as they identify cancer cells [2] [6] [7] [8]. Alternatively, a set of reference amplitudes and phases as they identify masses of benign cells can be used.

Figure 4:
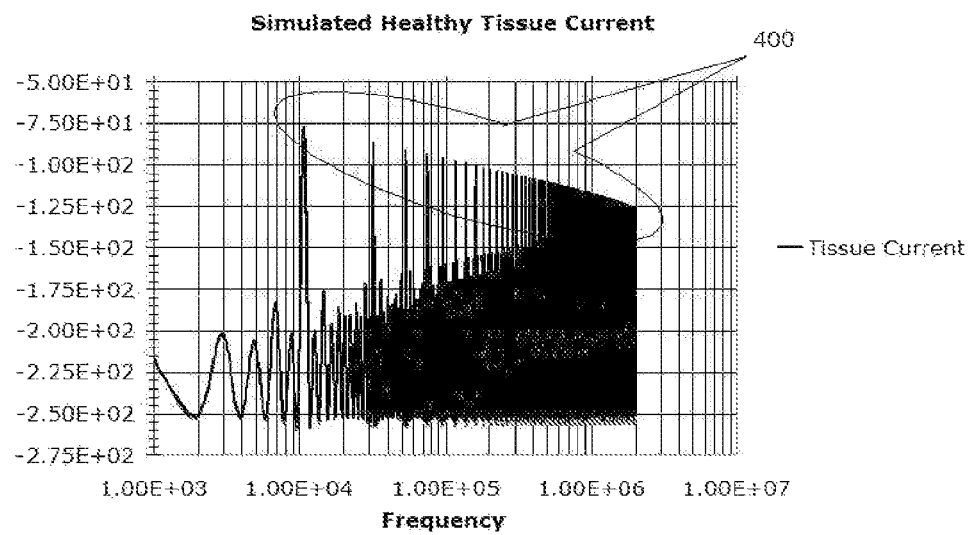
FIG. 4 illustrates the magnitude response of regular breast tissue.
Figure 5:
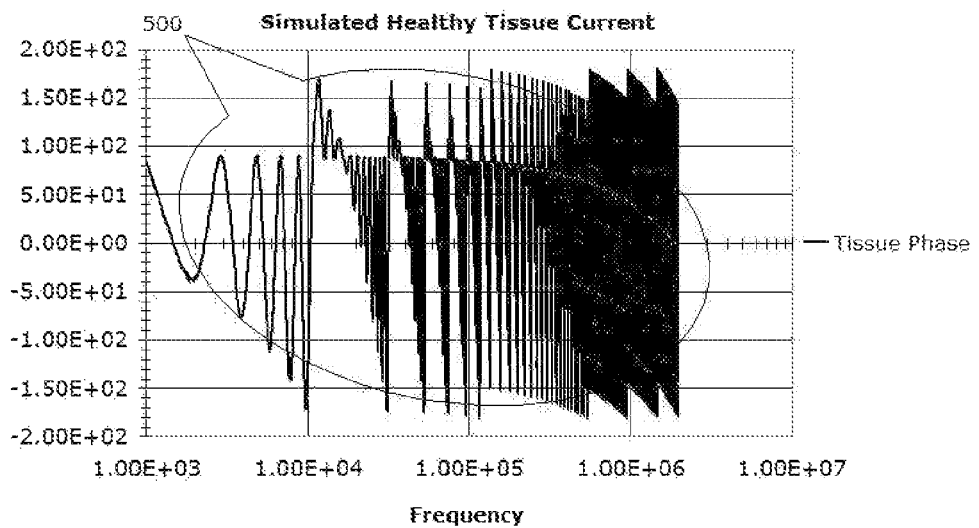
FIG. 5 shows the phase response of a regular breast tissue.
Figure 6:
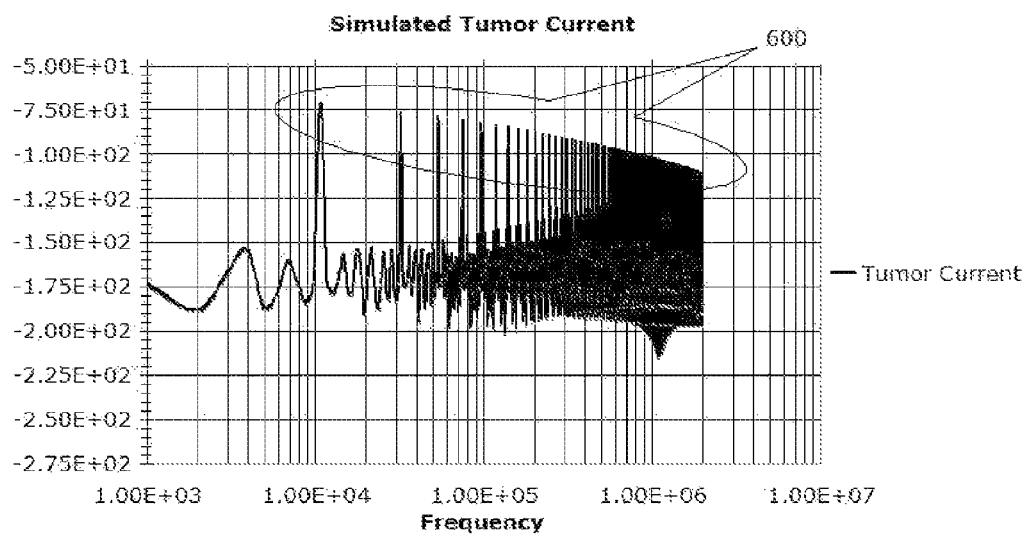
FIG. 6 illustrates the magnitude response of tumor tissue.
Figure 7:
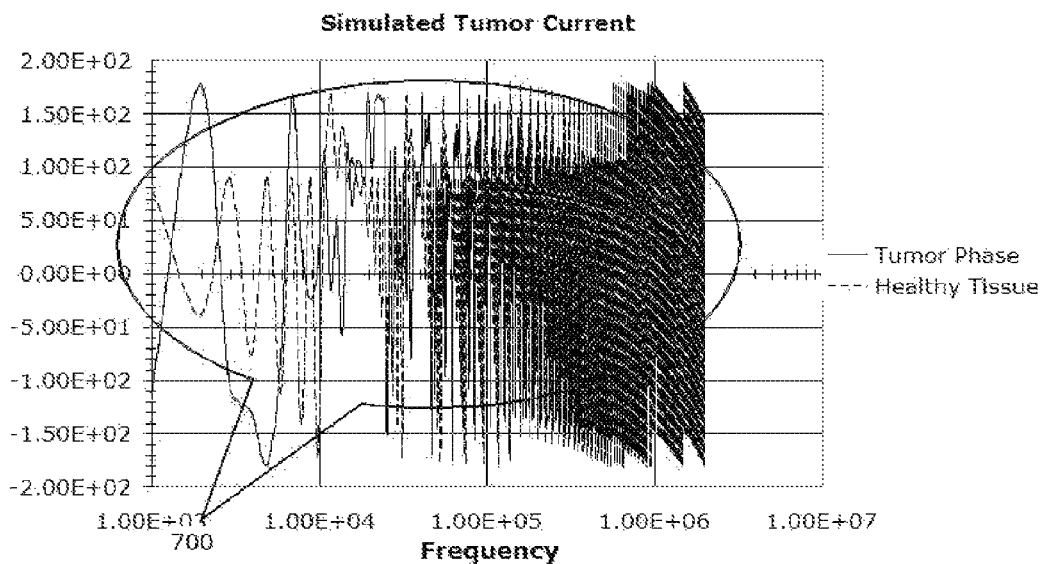
FIG. 7 shows the phase response of a regular and tumor tissue.

FIG. 4 shows an example of breast-tissue current with its magnitude response to the square-wave stimulus and FIG. 5 with its phase response. The model of a tumor tissue includes a non-linear capacitor. The harmonic level 400 in FIG. 4 is shifted to larger value. The phase plot 500 in FIG. 5 has changed shape. FIGS. 6 and 7 respectively show examples of breast-tissue current in magnitude 600 in FIG. 6 and phase responses to the square-wave stimulus for malignant breast tissue. FIG. 7 compares healthy tissue response with tumor tissue response 700.

The phase and amplitude changes across multiple frequencies differentiate the tissue into healthy cells, benign mass, and malignant tumor. The amount of phase shift at particular frequencies creates a marker to be identified during clinical studies. Having in excess of 40 harmonics, the cell signature makes the differentiation very visible.

Figure 8:
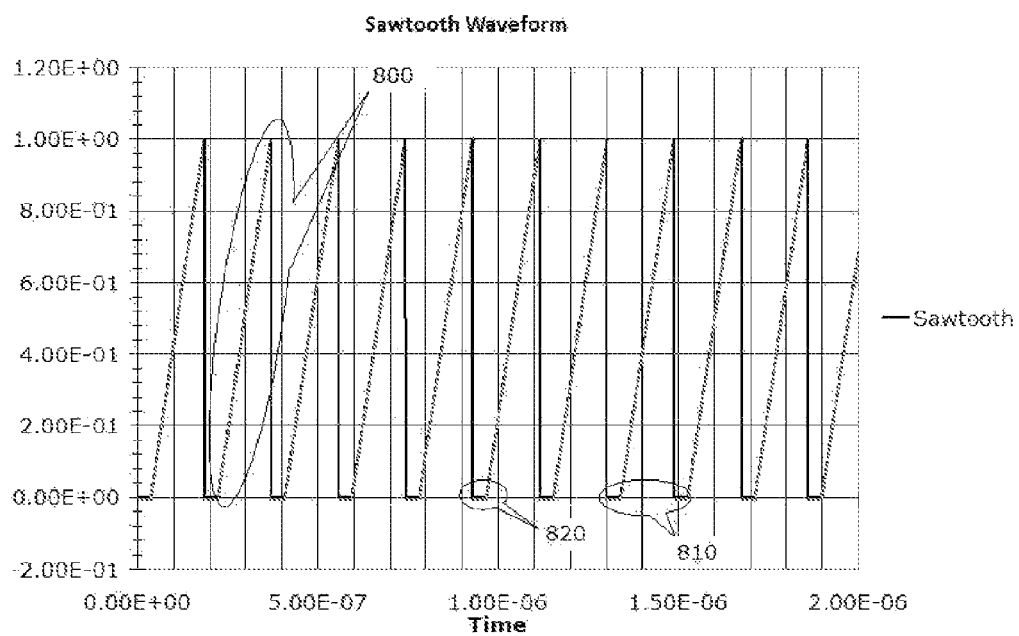
FIG. 8 shows saw tooth waveform.

Some of the scientific publications show analysis of dielectric properties of tumor cell in the frequency range up to 10 GHz. A modified saw tooth waveform 800 in FIG. 8 with coherent ratio between its period 810 and sampling interval would cover this range. The plateau 820 in the saw tooth could be made variable to tune in into the response of specific tumor cells.

Figure 9:
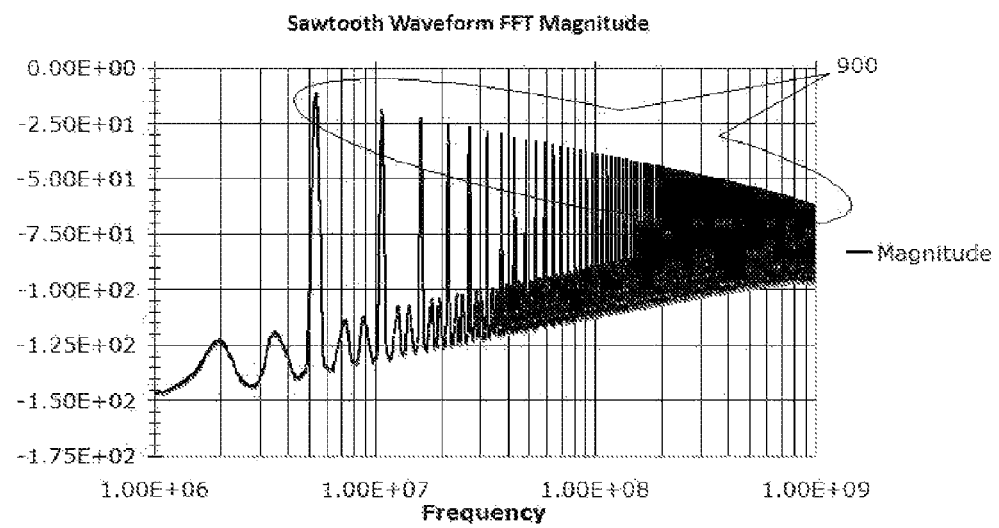
FIG. 9 shows the FFT magnitude of the saw tooth waveform.
Figure 10:
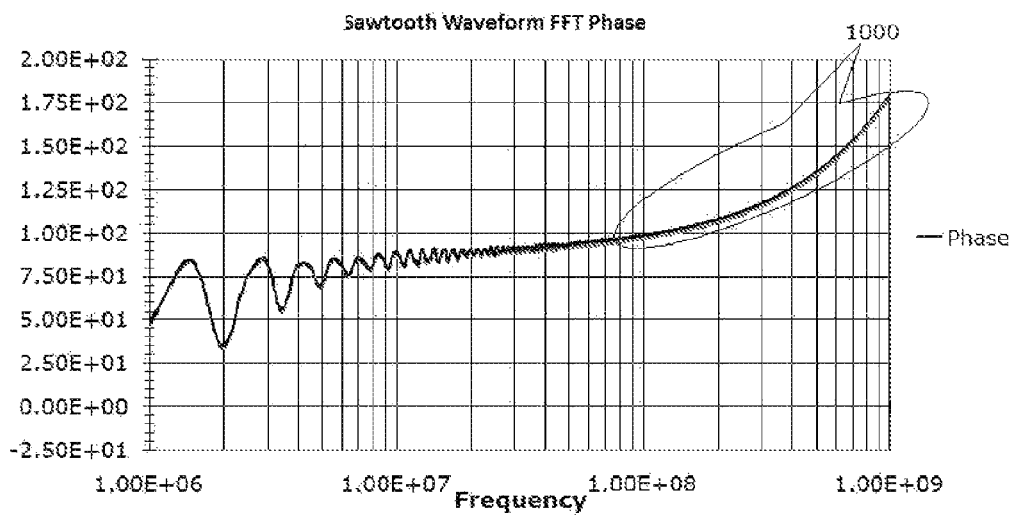
FIG. 10 shows the FFT phase of the saw tooth waveform.

The magnitude of Fast Fourier Transform is shown on FIG. 9. The waveform shows both even and odd harmonics 900. The phase response of the saw tooth waveform shown in FIG. 10 exhibits small variations in the bandwidth of interest 1000.

The waveform sources are distributed around the breast 1100 in a constant angular angle as shown in FIG. 11. The nipple is used to connect the detector 1110. The connection can be made via a cap or other surface connection or via an inserted probe. Generating waveforms and collecting data is done by stand-alone device 1120. The resulting data is transferred to a computer 1130 for visual and mathematical analysis. The receiving electrode in FIG. 11 may be one covering the nipple, or for increased localization capability may be an electrode made of insulated wire with a bare conducting tip inserted into one of the (typically on the order of nine). For differentiated signatures, this approaches permits greater localization. In another embodiment the source and receiving electrodes are incorporated in a brasserie.

The ECG/EKG pads are distributed in the area where breast attaches to the chest wall. The ECG/EKG pads can be replaced with 30 gauge needles to achieve a higher degree of accuracy.

The system is not limited to the use of a square wave. A sine wave can be used with the same coherent setting for multiple frequencies covering similar or the same harmonics. There could be one sine wave source with a non-linear gain element creating harmonics without need to step the frequencies.

Analyzing magnitude and phase for over 40 harmonics in frequency span from 10 kHz to 1 MHz will be a substantial source for the signature differentiating dielectric properties of healthy tissues versus tumor tissue. Many publications show Cole-Cole charts with significant changes when tumor cell start to grow in this frequency span.

In other embodiments, the number of source electrodes is varied. The larger the number of source electrodes, the higher the resolution of localization. For example having eight source electrodes arranged around the perimeter of the breast will double the localization capability since the area of the breast will be divided into eight regions as opposed to quadrants. Where in some applications of the device, one only wants to do screening to know whether a lesion is likely present or not, in others being able to localize would be important. This may occur, for example, if one is tracking changes in the lesion.

Feedback to the user as to results may take multiple forms. In one embodiment, the presence an abnormality is a non-visual feedback. This is supplied by an auditory or vibratory cue. Tone patterns can provide either a binary or relative magnitude, including level of probability. In another embodiment, the presence of an abnormality is indicated by a simple visual cue such as an LED display, either binary or relative magnitude, including level of probability.

In another embodiment, the presence of an abnormality is indicated by an intermediate visual display presenting text or graphical results, including level of probability. In still another embodiment, the presence of an abnormality is indicate by a complex visual display presenting raw data and processed graphical information, including level of probability.

The invention can be used as a screening device for initial, non-radiation involving, low-cost exam where, if the result is positive, a higher functionality version of the invention is used (for example, one with full display capabilities) and/or other techniques such as mammography, Magnetic Resonance Imaging, Positrode Emission Tomography, and ultrasound. For screening purposes it is usually important to adjust the detection level so that the results are biased to having false positives and avoiding false negatives since the false positive tests can be followed up more intensively, or, in some cases, by repetition of the initial type of test. One can adjust relationships among true positives and negatives and false positives and negatives. Specificity and sensitivity can be adjusted as well.

An important approach to the testing of such devices is the ability of comparing the healthy tissue in one breast to a potential lesion in the other breast in the same patient.

While the approach described is applied to breast tissue, the same techniques with the same parameters can be applied for detecting abnormalities in other tissues, including, but not limited to, for example, lung and prostate tissue, using suitable source and receiving electrodes.

It is noted that any embodiment described herein for exemplary purposes is, of course, subject to variations. Because variations and different embodiments may be made within the scope of the inventive concept(s) herein taught, it is to be understood that the details herein are to be interpreted as illustrative and not in a limiting sense.

The invention claimed is:

1. A device for testing presence and tracking of benign or malignant breast masses, the device including comprising:
   a. signal generator configured to deliver simultaneous stimuli at multiple frequencies with one or a plurality of source electrodes configured for attachment where a breast joins the chest wall of a patient,
   b. a receiving electrode adapted for configured for attachment to the nipple of the same breast;
   c. a computer program stored on a non-transient medium executed by a control system,
   d. the control system configured to use the simultaneously occurring multi-frequencies coherent signals applied in a sequence to each source electrode to stimulate tissue through;
   e. the control system configured to use ratio-metric measurements and coherent sampling across simultaneously occurring signals in returning current from the tissue;
   f. the control system configured to determine ratio measurements where the measurements examines the interaction between multiple-frequencies amplitudes and phases, not the absolute values;
   g. the control system configured to use derived ratios created in clinical studies of tissue to determine a classification result of the determined ratio measurements of tissue selected from the group consisting of healthy, benign, and malignant tissue; and
   h. the control system configured to use an indicator that indicates the results to the user.

2. The device of claim 1 where a wide spectral band is used from 20 kHz to 1 MHz with even and odd harmonics coherently sampled between the output stage and wide-band current input measurement input.

3. The device of claim 1 where a wide spectral band is used from 1 MHz to 100 MHz with even and odd harmonics coherently sampled between the output stage and wide-band current input measurement input.

4. The device of claim 1 where a wide spectral band is used from 100 MHz to 10 GHz with even and odd harmonics coherently sampled between the output stage and wide-band current input measurement input.

5. The device of claim 1 where the excitation wave form is selected from the group consisting of square wave, sine wave, and triangle wave.

6. The system of claim 1 where the receiving electrode is a wire inserted into one of the milk ducts.

7. The device in claim 1 in which the number source electrodes is selected from the group consisting of 4, 6, 8, 12, and 16.

8. The device in claim 1 in which the electrodes are incorporated into a brassiere.

9. The device in claim 1 where the presence of an abnormality is indicated by a non-visual feedback selected from the group consisting of auditory cue and vibratory cue.

10. The device in claim 1 where the presence of an abnormality is a simple visual cue such as an LED display, either binary or relative magnitude, including level of probability.

11. The device in claim 1 where the presence of an abnormality is an intermediate visual display presenting text or graphical results, including level of probability.

12. The device in claim 1 where the presence of an abnormality is a complex visual cue display presenting raw data and processed graphical information, including level of probability.

13. The device in claim 1 used in screening where if a result is positive, confirmation is sought by use of a technique selected from the group consisting of mammography, Magnetic Resonance Imaging, Positron Emission Tomography, and ultrasound.

14. The device in claim 1 where tissue in one breast is compared to a potential lesion in the other breast in the same patient.

15. The device in claim 1 where adjustments are made in specificity and sensitivity.

16. The device in claim 1 where adjustments are made in parameters selected from the group consisting of true positives, false positives, true negatives, and false negatives.

17. The device in claim 1 where the presence of an abnormality is stored and accessed by medical professional through computer or internet.

* * * * *

UNITED STATES PATENT AND TRADEMARK OFFICE
CERTIFICATE OF CORRECTION

| | |
|---|---|
| PATENT NO. | : 9,037,227 B2 |
| APPLICATION NO. | : 12/874192 |
| DATED | : May 19, 2015 |
| INVENTOR(S) | : Roman A. Slizynski and David J. Mishelevich |

Page 1 of 1

It is certified that error appears in the above-identified patent and that said Letters Patent is hereby corrected as shown below:

In the drawings delete Fig. 1, and replace with the following:

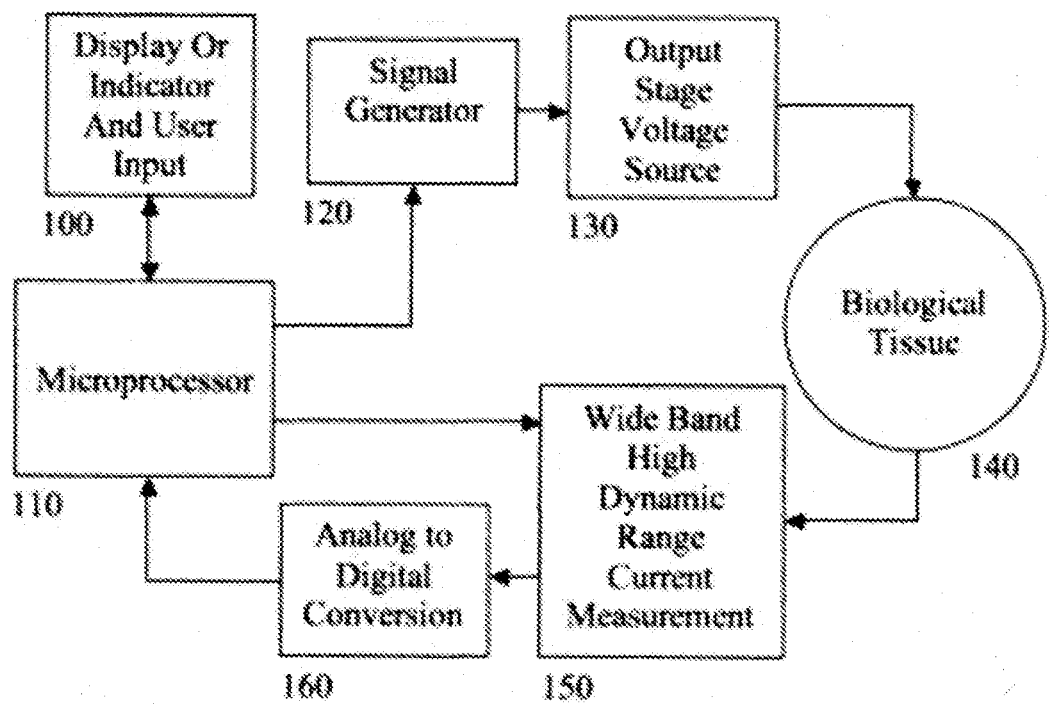

FIG. 1

Signed and Sealed this
Twentieth Day of October, 2015

Michelle K. Lee
*Director of the United States Patent and Trademark Office*